US010682441B2

(12) United States Patent
Gil et al.

(10) Patent No.: US 10,682,441 B2
(45) Date of Patent: Jun. 16, 2020

(54) SELF-ASSEMBLING PEPTIDES COMPRISING NON-IONIC POLAR AMINO ACIDS

(71) Applicant: 3-D Matrix, Ltd., Tokyo (JP)

(72) Inventors: Eun Seok Gil, Acton, MA (US); Marc Rioult, Fontaines-sur-Saône (FR); Keiji Nagano, Tokyo (JP); Karl Partick Gilbert, Danvers, MA (US); Toshiro Kiyofuji, Tokyo (JP); Yuya Hasegawa, Tokyo (JP)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 15/534,715

(22) PCT Filed: Dec. 11, 2015

(86) PCT No.: PCT/US2015/065302
§ 371 (c)(1),
(2) Date: Jun. 9, 2017

(87) PCT Pub. No.: WO2016/094829
PCT Pub. Date: Jun. 16, 2016

(65) Prior Publication Data
US 2017/0360990 A1 Dec. 21, 2017

Related U.S. Application Data

(60) Provisional application No. 62/091,130, filed on Dec. 12, 2014.

(51) Int. Cl.
*A61L 27/54* (2006.01)
*C07K 7/08* (2006.01)
*A61L 27/52* (2006.01)
*A61L 27/22* (2006.01)
*C07K 14/00* (2006.01)

(52) U.S. Cl.
CPC ............. *A61L 27/52* (2013.01); *A61L 27/227* (2013.01); *A61L 27/54* (2013.01); *C07K 7/08* (2013.01); *C07K 14/001* (2013.01); *A61L 2300/25* (2013.01)

(58) Field of Classification Search
CPC combination set(s) only.
See application file for complete search history.

(56) References Cited
U.S. PATENT DOCUMENTS

2003/0215950 A1* 11/2003 Lasure ................ C07H 21/04
435/483
2009/0130455 A1 5/2009 Mirkin et al.
2011/0318380 A1 12/2011 Brix et al.
2014/0273148 A1 9/2014 Collier et al.

FOREIGN PATENT DOCUMENTS

| CN | 102688525 | 9/2012 |
| WO | WO 2010/037395 | 4/2010 |
| WO | 2012016357 A1 | 2/2012 |
| WO | 2014167350 A1 | 10/2014 |
| WO | WO 2016/094829 | 6/2016 |

OTHER PUBLICATIONS

Rambaran et al., Prion, 2008; vol. 2 Issue 3, 112-117. (Year: 2008).*
Luhrs et al., PNAS, 2005, vol. 102, No. 17342-17347. (Year: 2005).*
NCBI, Chain A, C99-Protein—NCBI, available online at https://www.ncbi.nlm.nih.gov/protein/2LP1_A?report=genbank&log$=protalign&blast_rank=16&RID=K28R4GYG015, accessed on Jul. 19, 2019. (Year: 2019).*
E Protopapa et al., "Interaction of self-assembling beta-sheet peptides with phospholipid monolayers: The effect of serine, threonine, glutamine and asparagine amino acid side chains," Electrochimica ACTA., vol. 55, pp. 3368-3375, XP26924586, Elsevier Science Publishers, Barking. ISSN: 0013-4686 (2010).
Paradossi et al., "Poly(vinyl alcohol) as versatile biomaterial for potential biomedical applications," Journal of materials science Materials in medicine, 2003, 14:687-91.
PCT International Search Report and Written Opinion in Appln. No. PCT/US2015/065302, dated Jun. 13, 2017, 10 pages.
Rafat et al., "Dual functionalized PVA hydrogels that adhere endothelial cells synergistically," Biomaterials, 2012, 33:3880-6.
Slieker et al., "Effects of new anti-adhesion polyvinyl alcohol gel on healing of colon anastomoses in rats," Surgical infections. 2012, 13:396-400.
Sun et al., "A self-assembling peptide RADA16-I integrated with spider fibroin uncrystalline motifs," International journal of nanomedicine, 2012, 7:571-80.
Ye et al., "Temperature and pH effects on biophysical and morphological properties of self-assembling peptide RADA16-I," Journal of peptide science : an official publication of the European Peptide Society. 2008, 14:152-62.
Bolduc et al., "Peptide self-assembled monolayers for label-free and unamplified surface plasmon resonance biosensing in crude cell lysate," Analytical Chemistry, American Chemical Society, Jul. 16, 2009, 81(16):6779-6788.

(Continued)

*Primary Examiner* — James H Alstrum-Acevedo
*Assistant Examiner* — Kaipeen E Yang
(74) *Attorney, Agent, or Firm* — Fish & Richardson P.C.

(57) ABSTRACT

Compositions, peptide solutions and macroscopic scaffolds of self-assembling peptides consisting essentially of non-ionic, polar amino acids are provided. Particular peptides include those comprising or consisting essentially of serine, threonine, tyrosine, cysteine, glutamine, asparagine, methionine, tryptophan, hydroxy-proline, and combinations thereof. Methods of sterilizing the self-assembling peptides, and scaffolds comprising the peptides are also provided.

35 Claims, 11 Drawing Sheets

Specification includes a Sequence Listing.

(56) References Cited

OTHER PUBLICATIONS

EP Office Action in European Appln. No. 15819990, dated Jun. 11, 2019, 7 pages.
CN Office Action in Chinese Appln. No. 201580074430, dated Nov. 6, 2019, 22 pages.

* cited by examiner

ST14

T14

SELF-ASSEMBLING PEPTIDES COMPRISING NON-IONIC POLAR AMINO ACIDS

CROSS-REFERENCE TO RELATED APPLICATIONS

This application is a U.S. national phase application and claims the benefit of priority under 35 U.S.C. § 371 of International Patent Application Serial No. PCT/US2015/065302 as filed on Dec. 11, 2015 and titled "SELF-ASSEMBLING PEPTIDES COMPRISING NON-IONIC POLAR AMINO ACIDS" which, in turn, claims priority under 35 U.S.C. § 119(e) to U.S. Provisional Patent Application Ser. No. 62/091,130 as filed on Dec. 12, 2014.

FIELD OF THE TECHNOLOGY

One or more aspects relate generally to materials and methods that may be used in medical and research applications. More particularly, one or more aspects relate to materials and methods that may be used to provide peptide hydrogel materials.

SEQUENCE LISTING

The instant application contains a Sequence Listing which has been submitted electronically in ASCII format and is hereby incorporated by reference in its entirety. Said ASCII copy, created on Dec. 19, 2018, is named 46406_0019US1_SL.txt and is 4 kilobytes in size.

SUMMARY

In accordance with one or more aspects, a composition comprising a self-assembling peptide consisting essentially of non-ionic, polar amino acids is provided.

In accordance with one or more aspects, a peptide solution comprising a self-assembling peptide consisting essentially of non-ionic, polar amino acids is provided.

In accordance with one or more aspects, a method of sterilizing peptides is provided. The method comprises providing a peptide solution comprising a self-assembling peptide consisting essentially of non-ionic, polar amino acids. The method also comprises treating the peptide solution at a predetermined temperature and a predetermined pressure for a predetermined period of time to sterilize the peptide solution, the predetermined temperature and predetermined pressure selected to provide conditions of saturated steam.

In accordance with one or more aspects, a macroscopic scaffold comprising self-assembling peptides consisting essentially of non-ionic, polar amino acids is provided.

BRIEF DESCRIPTION OF THE DRAWINGS

The accompanying drawings are not intended to be drawn to scale. For purposes of clarity, not every component may be labeled. In the drawings.

DETAILED DESCRIPTION

Figure 1:
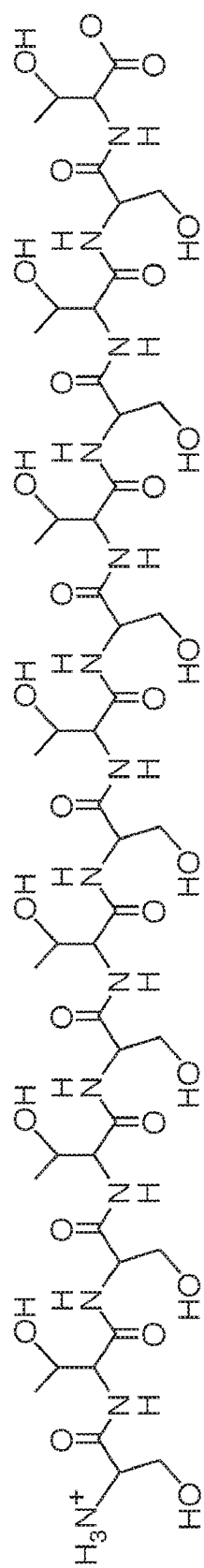
FIG. 1 is a chemical structure of ST14 (SEQ ID NO: 2), in accordance with some embodiments.

In accordance with one or more embodiments, self-assembling peptides are provided comprising non-ionic, polar amino acids. The term "self-assembling peptide" may refer to a peptide that may exhibit a beta-sheet structure in aqueous solution in the presence of specific conditions to induce the beta-sheet structure. The specific conditions may include adjusting the pH of a self-assembling peptide solution. The adjustment may be an increase or a decrease in the pH of the self-assembling peptide solution. The adjustment of pH may be an adjustment, for example, an increase or decrease, in pH to a physiological pH or a neutral pH. The specific conditions may also include adding a cation, such as a monovalent cation, to a self-assembling peptide solution.

"Physiological conditions," such as a physiological pH or a physiological temperature, may occur in nature for a particular organism, cell system, or subject which may be in contrast to artificial laboratory conditions. The conditions may comprise one or more properties such as one or more particular properties or one or more ranges of properties. For example, the physiological conditions may include a temperature or range of temperatures, a pH or range of pH's, a pressure or range of pressures, and one or more concentrations of particular compounds, salts, and other components. For example, in some examples, the physiological conditions may include a temperature in a range of about 20 to about 40 degrees Celsius. In some examples, the atmospheric pressure may be about 1 atm. The pH may be in the range of a neutral pH. For example, the pH may be in a range of about 6 to about 8. In some instances, the physiological pH may be less than 6, for example, about 1-4, in the case of at least a portion of the gastric tract.

The physiological conditions may include cations such as monovalent metal cations that may induce membrane or hydrogel formation. These may include sodium chloride (NaCl). The physiological conditions may also include a glucose concentration, sucrose concentration, or other sugar concentration, of between about 1 mM and about 20 mM. The physiological conditions may include the local conditions of the target site in some specific embodiments.

The self-assembling peptides may be referred to as or be a part of a composition, which may be a hydrogel, for example, a hydrogel scaffold. In accordance with one or more embodiments, self-assembling peptides are provided consisting essentially of non-ionic, polar amino acids. In yet other embodiments, self-assembling peptides are provided consisting of non-ionic, polar amino acids. Compositions or peptide solutions may be provided that comprise, consist essentially of, or consist of a self-assembling peptide.

The number or percentage of specific non-ionic, polar amino acids may be based on the peptide's ability to self-assemble. The compositions and peptide solutions may comprise or consist essentially of, or consist of self-assembling peptides consisting essentially of non-ionic, polar amino acids.

In some embodiments, the non-ionic polar amino acids of the self-assembling peptide may be selected from the group consisting of serine, threonine, tyrosine, cysteine, glutamine, asparagine, methionine, tryptophan, hydroxyl-proline, and combinations thereof. The non-ionic polar amino acids of the self-assembling peptide may be selected from the group consisting of serine and threonine. The non-ionic, polar amino acids of the self-assembling peptide may consist essentially of threonine.

In certain embodiments, the self-assembling peptide, may have, comprise, consist essentially of, or consist of a number of amino acids, or have a peptide length, that provides for self-assembling of the peptide. The self-assembling peptide may be longer than that length that may provide self-assembly of the peptide, although in certain instances it may not be desirable due to cost or aggregation of the peptides during or after self-assembly.

In certain embodiments, the self-assembling peptide may have, comprise, or consist essentially of between about 7 amino acids and about 200 amino acids. The self-assembling peptide may consist essentially of between about 7 amino acids and about 200 amino acids. The self-assembling peptide may consist essentially of about 7 amino acids. The self-assembling peptide may consist essentially of about 8 amino acids. The self-assembling peptide may consist essentially of about 10 amino acids. The self-assembling peptide may consist essentially of about 12 amino acids. The self-assembling peptide may consist essentially of about 14 amino acids. The self-assembling peptide may consist essentially of about 16 amino acids. The self-assembling peptide may consist essentially of about 18 amino acids. The self-assembling peptide may consist essentially of about 20 amino acids.

In some embodiments, the self-assembling peptide may comprise, consist essentially of, or consist of alternating non-ionic, polar amino acids. The self-assembling peptide, or the alternating non-ionic, polar amino acid portion of the peptide, may be of an appropriate or pre-determined length as described above.

By alternating, it is meant to include a series of three or more amino acids that alternate between a first non-ionic, polar amino acid and a second non-ionic, polar amino acid. In some embodiments, alternating is meant to include a series of three or more amino acids that alternate between a first non-ionic, polar amino acid, a second, non-ionic polar amino acid, and a third non-ionic, polar amino acid. In some embodiments, alternating is meant to include a series of four or more amino acids that alternate between a first non-ionic, polar amino acid, a second, non-ionic polar amino acid, a third non-ionic, polar amino acid, and a fourth non-ionic, polar amino acid. It need not include each and every amino acid in the peptide sequence alternating between a first non-ionic, polar amino acid and a second non-ionic, polar amino acid, or alternating between a first non-ionic, polar amino acid, a second non-ionic, polar amino acid, and a third non-ionic, polar amino acid, or alternating between a first non-ionic, polar amino acid, a second non-ionic, polar amino acid, a third non-ionic, polar amino acid, and a fourth non-ionic, polar amino acid.

In some embodiments, a self-assembling peptide may be provided that comprises, consists essentially of, or consists of consecutive non-ionic polar amino acids. The self-assembling peptide, or the consecutive non-ionic, polar amino acid portion of the peptide, may be of an appropriate or pre-determined length as described above.

By consecutive, it is meant to include a series of three or more amino acids that follow continuously, in unbroken succession. In certain embodiments, self-assembling peptides may be provided that comprise non-ionic, polar amino acids in a consecutive arrangement. For example, a self-assembling peptide may comprise consecutive non-ionic, polar amino acids. The non-ionic, polar amino acids that are consecutive may be the same non-ionic, polar amino acid. In some instances, the non-ionic, polar amino acids that are consecutive may be different from one another, but may maintain a repetitive pattern.

In some embodiments, the self-assembling peptide may comprise, consist essentially of, or consist of alternating non-ionic, polar amino acids. The alternating non-ionic, polar amino acids may be alternating serine and threonine amino acids. In some embodiments, the self-assembling peptide may comprise alternating amino acids of serine and threonine. In other embodiments, the self-assembling peptides may consist essentially of alternating amino acid residues of serine and threonine. In certain embodiments, a self-assembling peptide consisting essentially of 14 non-ionic, polar amino acids, alternating between serine and threonine is provided, in certain instances, referred to as ST14.

In some embodiments, a self-assembling peptide is provided consisting essentially of consecutive non-ionic, polar amino acids. In some embodiments, a self-assembling peptide is provided consisting essentially of threonine amino acids. The composition may consist essentially of at least 7 threonine amino acids. The self-assembling peptide may consist essentially of 14 threonine amino acids. In certain embodiments, the self-assembling peptide may consist essentially of at least 14 threonine amino acids. The self-assembling peptide may consist essentially of 14 non-ionic, polar threonine amino acids is provided, which may be referred to as T14.

ST14 and T14 are composed of amino acids with polar uncharged side chains, specifically serine (Ser or S) and threonine (Thr or T). The side chain of serine is a primary alcohol, chemically equivalent to a substituted methanol. Also, the side chain of threonine contains a secondary alcohol and a methyl group. Considering the side groups, ST14 and T14 are similar to polyvinyl alcohol (PVC), where the side group is a primary alcohol like serine. PVC has been used in biomedical applications for its biocompatibility.

ST14 is composed of serine and threonine, which are alternately sequenced to have fourteen amino acids in the structure, as shown below and in FIG. 1.

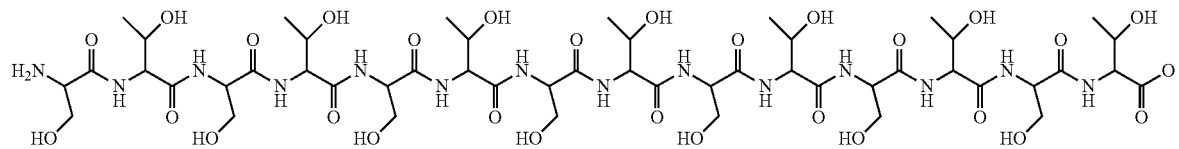 [SMILES: CC(O)C(NC(=O)C(CO)NC(=O)C(NC(=O)C(CO)NC(=O)C(NC(=O)C(CO)NC(=O)C(NC(=O)C(CO)NC(=O)C(NC(=O)C(CO)NC(=O)C(NC(=O)C(CO)NC(=O)C(NC(=O)C(N)CO)C(C)O)C(C)O)C(C)O)C(C)O)C(C)O)C(C)O)C(=O)O]

FIG. 1. Chemical structure of ST14 (SEQ ID NO: 2). ST14 (SEQ ID NO: 2) has fourteen alternating serines and threonines in its structure.

T14 is composed of only threonine, where fourteen threonines are sequenced consecutively in the structure, as shown below and in FIG. 2.

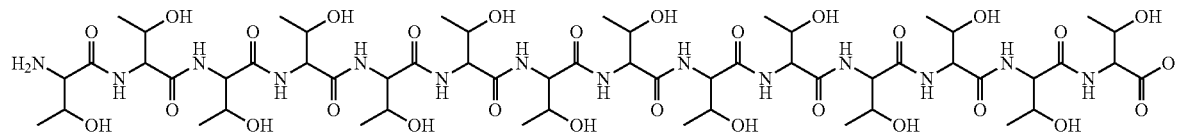 [SMILES: CC(O)C(N)C(=O)NC(C(=O)NC(C(=O)NC(C(=O)NC(C(=O)NC(C(=O)NC(C(=O)NC(C(=O)NC(C(=O)NC(C(=O)NC(C(=O)NC(C(=O)NC(C(=O)NC(C(=O)O)C(C)O)C(C)O)C(C)O)C(C)O)C(C)O)C(C)O)C(C)O)C(C)O)C(C)O)C(C)O)C(C)O)C(C)O)C(C)O]

Figure 2:
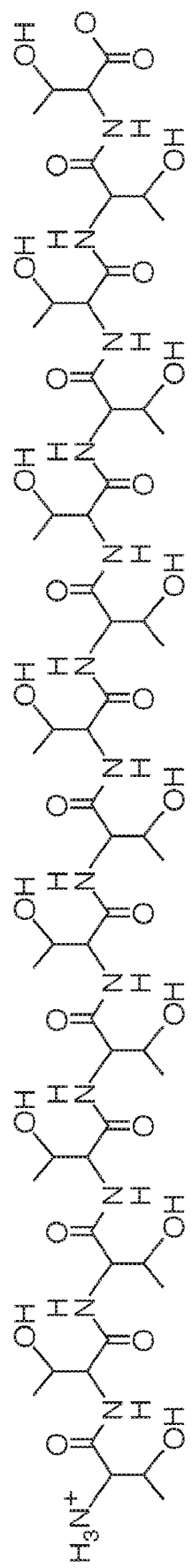
FIG. 2 is a chemical structure of T14 (SEQ ID NO:1), in accordance with some embodiments.

FIG. 2. Chemical structure of T14 (SEQ ID NO: 1). T14 (SEQ ID NO: 1) has fourteen consecutive threonines in its structure.

The compositions, peptide solutions, and self-assembling peptides of the present disclosure may be capable of forming self-assembled nanofibers.

Peptide solutions may be provided comprising, consisting essentially of, or consisting of, the compositions or self-assembling peptides of the present disclosure. For example, peptide solutions may be provided comprising, consisting essentially of, or consisting of self-assembling peptides consisting essentially of, or consisting of, non-ionic, polar amino acids. Peptide solutions may be provided that may comprise a number of non-ionic, polar amino acids to provide for self-assembly of the peptides. The number of non-ionic, polar amino acids may be based on its ability to self-assemble. The peptide solutions may comprise, consist essentially of, or consist of any of the self-assembling peptides described herein.

In some embodiments, a peptide solution may be provided comprising, consisting essentially of, or consisting of a composition or a self-assembling peptide comprising, consisting essentially of, or consisting of alternating amino acid residues of serine (S) and threonine (T). A peptide solution may be provided comprising, consisting essentially of, or consisting of a composition or self-assembling peptide consisting essentially of alternating amino acid residues of serine (S) and threonine (T) or a composition consisting essentially of 14 or more threonine amino acids.

The concentration of the self-assembling peptide in the peptide solution may be between about 0.1 weight per volume (w/v) percent to about 10 weight per volume (w/v) percent. In certain embodiments, the concentration of self-assembling peptide in the peptide solution is between about 0.5 weight per volume (w/v) percent and about 5 weight per volume (w/v) percent.

The pH of the peptide solution (of peptide in deionized water) may be between about 1.5 and about 3. In certain embodiments, the pH of the peptide solution may be between about 1.8 and about 2.7. In certain embodiments, the pH of the peptide solution may be between about 1.9 and 2.5. The pH of the peptide solution may vary depending upon various properties of the peptide, including the type of amino acids, length of peptide, and concentration of peptide in the solution.

In certain embodiments, the peptide solution may have a pH of between about 0.5 and about 8. The pH of the peptide solution may be adjusted to provide a peptide solution having a pH of between about 0.5 to about 8. In certain embodiments, the pH of the peptide solution may be adjusted to be between about 3 and about 8. The peptide solution may be changed or adjusted based on its desired use. For example a more neutral (a pH of between about 5 and 8) may be desirable for particular applications, for example, laboratory experiments. The same or different range of pH values may be desirable for other applications. The peptide solution may be substantially non-biologically active.

The peptide solution may have a storage modulus that increases by exposing the solution to conditions of higher pH. For example, by exposing the peptide solution to a pH of between about 7 and about 8, or to a neutral pH, the storage modulus may increase between about 5 to about 10 times. The exposure may occur for a predetermined time. For example, the exposure may occur for a time of about 30 seconds to about 60 minutes, or about 1 minute to about 30 minutes, or about 2 minutes to about 15 minutes. In some embodiments, the exposure may be for an indefinite period of time. In some embodiments the storage modulus of the peptide solution may increase about 7 times after exposure to a pH of between about 7 and about 8, or to a neutral pH. In certain embodiments, the concentration of peptide in the peptide solution is between about 0.1 weight per volume (w/v) percent and about 10 weight per volume (w/v) percent. In certain embodiments, the concentration of peptide in the peptide solution is between about 0.5 weight per volume (w/v) percent and about 5 weight per volume (w/v) percent. The concentration of the peptide solution may be about 1 (w/v) percent peptide.

In certain embodiments, the peptide solutions of the present disclosure may comprise cells. The cells may be, or may be derived from humans or other mammals. In certain embodiments, the cells may be mesenchymal stem cells. In some embodiments, the cells may be mouse mesenchymal stem cells. In some embodiments, the cells may be human mesenchymal stem cells. The concentration of cells in the solution may be about 5 million cells per milliliter. In some embodiments, the cell concentration may be less than 5 million cells per milliliter.

In certain other embodiments, the peptide may comprise, consist essentially of, or consist of at least about 14 amino acids. The peptide may be TTTTTTTTTTTTTT (T14) (SEQ ID NO: D. The peptide may be STSTSTSTSTSTST (ST14) (SEQ ID NO: 2).

The hydrogel scaffold may be characterized by a storage modulus of greater than about 10 Pa. In certain embodiments, the hydrogel scaffold may be characterized by a storage modulus of greater than about 100 Pa. This may be determined, at least in part, by the concentration of the initial peptide solution. For example, in certain embodiments, without wishing to be bound by theory, the greater the concentration of the initial peptide solution, the higher the storage modulus of the hydrogel scaffold.

The concentration effective to form a hydrogel scaffold may comprise a concentration in a range of between about 0.5 weight per volume (w/v) percent and about 5 weight per volume (w/v) percent.

The hydrogel scaffold may have nanofibers having a diameter of between about 1 nanometer and about 20 nanometers. In certain embodiments, the hydrogel scaffold may comprise nanofibers having a diameter of less than about 5 nanometers.

In certain embodiments, the self-assembling peptides of the present disclosure, for example self-assembling peptides consisting essentially of, or consisting of, non-ionic, polar amino acids are characterized by having stability (little or no degradation), or little or no change in molecular weight after being autoclaved. The autoclaving process may be performed on the self-assembling peptide or self-assembling peptide solution, and may provide for a successful sterilization of the self-assembling peptide or self-assembling peptide solution with minimal or no degradation of the self-assembling peptide. Sterilization refers to a process that eliminates or kills at least a portion of microorganisms present, and may include elimination or reduction of at least a portion of all forms of life, including transmissible agents, such as microorganisms, fungi, bacteria, viruses, and spores, present in a fluid, compound, or material. Sterilization may include an elimination or reduction in microorganisms that would be suitable for its intended use. Sterilization may include an at least about 50%, 60%, 70%, 80%, 90%, 95%, 97%, 98%, 99%, 99.5%, 99.9%, elimination or reduction of all forms of life, including transmissible agents, such as microorganisms, fungi, bacteria, viruses, and spores, present in a fluid, compound, or material. Sterilization may include a 100% elimination or reduction of all forms of life, including transmissible agents, such as microorganisms, fungi, bacteria, viruses, and spores present. The autoclaving process may be performed using any conventional autoclaving procedure, for example at 121° C. at saturated steam for a predetermined period of time. The time for autoclaving may be between about 1 minute and about 30 minutes. In certain embodiments, the predetermined time may be at least about 3 minutes. In certain embodiments, the predetermined time may be at least about 15 minutes. In certain other embodiments, the predetermined time may be at least about 25 minutes. The successful autoclaving of these peptides provides a consistent procedure for sterilizing the self-assembling peptides and peptide solutions of any concentration, and avoids potential problems that may occur with filtering peptide solutions of higher concentrations. Particular self-assembling peptides that have stability during the autoclaving process include those of the present disclosure, including ST14 and T14.

Methods may be provided for sterilizing self-assembling peptides of the present disclosure. The method may comprise providing a self-assembling peptide, or a self-assembling peptide solution, comprising a self-assembling peptide of the present disclosure. The peptide solution may comprise, or consist essentially of a self-assembling peptide consisting essentially of, or consisting of non-ionic, polar amino acids. The peptide solution may comprise or consist essentially of a self-assembling peptides comprising at least one of a self-assembling peptide consisting essentially of threonine, and a peptide consisting essentially of alternating serine and threonine. The method may comprise treating the peptide solution at a predetermined temperature and a predetermined pressure for a predetermined period of time to sterilize the peptide solution, the predetermined temperature and predetermined pressure selected to provide conditions of saturated steam.

The method may further comprise measuring the molar mass of the self-assembling peptide in the peptide solution prior to treating the peptide solution. The method may further comprise measuring the molar mass of the self-assembling peptide in the peptide solution subsequent to treating the peptide solution. The method may further comprise comparing the molar mass of the self-assembling peptide in the peptide solution prior to treating the peptide solution, with the molar mass of the self-assembling peptide in the peptide solution subsequent to treating the peptide solution. Treating the peptide solution may comprise treating the peptide solution in an autoclave.

As discussed, the temperature and pressure may be selected to provide conditions of saturated steam. For example, the temperature may be about 121° C. and the pressure may be about 15 psi. The temperature may be about 132° C. and the pressure may be about 30 psi.

The predetermined period of time may be between about 1 minute and about 30 minutes. In certain embodiments, the predetermined time may be at least about 3 minutes. In certain embodiments, the predetermined time may be at least about 15 minutes. In certain other embodiments, the predetermined time may be at least about 25 minutes.

Exemplary conditions may include those in Table 1.

TABLE 1

| Temperature | Pressure | Time |
| --- | --- | --- |
| 121° C. | 15 psi | 25 minutes |
| 121° C. | 15 psi | 15 minutes |
| 132° C. | 30 psi | 3 minutes |
| 132° C. | 30 psi | 8 minutes |
| 132° C. | 30 psi | 10 minutes |

In this regard, peptide solutions or self-assembling peptides of this disclosure may be provided that have been sterilized by autoclaving.

Sterilization by gamma irradiation may also be performed on the peptide or peptide solution. Peptides or peptide solutions of this disclosure may be provided that have been sterilized by gamma irradiation.

In accordance with one or more embodiments, a macroscopic scaffold is provided. The macroscopic scaffold may comprise, consist essentially of, or consist of a plurality of self-assembling peptides, each of which comprises, consists essentially of, or consists of between about 7 and about 200 non-ionic, polar amino acids. The peptides may comprise, consist essentially of, or consist of between about 8 to about 20 amino acids. The peptides may consist essentially of non-ionic, polar amino acid residues. The non-ionic polar amino acids of the self-assembling peptide may be selected from the group consisting of serine, threonine, tyrosine, cysteine, glutamine, asparagine, methionine, tryptophan, and hydroxyl-proline, and combinations thereof. The macroscopic scaffold may comprise, consist essentially of, or consist of any of the self-assembling peptides discussed in this disclosure.

In some embodiments, a biologically active agent may be used with the materials and methods of the present disclosure, and may be part of the compositions and peptide solutions disclosed herein. A biologically active agent may comprise a compound, including a peptide, DNA sequence, chemical compound, or inorganic or organic compound that may impart some activity, regulation, modulation, or adjustment of a condition or other activity in a subject or in a laboratory setting. The biologically active agent may interact with another component to provide such activity. The biologically active agent may be referred to as a drug in accordance with some embodiments herein. In certain embodiments, one or more biologically active agents may be gradually released to the outside of the peptide system. For example, the one or more biologically active agents may be gradually released from the hydrogel. Both in vitro and in vivo testing has demonstrated this gradual release of a biologically active agent. The biologically active agent may be added to the peptide solution prior to administering to a subject, or may be administered separately from the solution to the subject.

This disclosure relates to aqueous solutions, compositions, hydrogels, scaffolds, and membranes comprising self-assembling peptides, sometimes referred to as self-assembling oligopeptides. The self-assembling peptides may exhibit a beta-sheet structure in aqueous solution in the presence of neutral pH, physiological pH, and/or a cation, such as a monovalent cation.

The peptides may be generally stable in aqueous solutions and self-assemble into large, macroscopic structures, scaffolds, or matrices when exposed to neutral or physiological pH. Once the hydrogel is formed it may not decompose, or may decompose or biodegrade after a period of time. The rate of decomposition may be based at least in part on at least one of the amino acid sequence and conditions of its surroundings.

By "macroscopic" it is meant as having dimensions large enough to be visible under magnification of 10-fold or less. In preferred embodiments, a macroscopic structure is visible to the naked eye. A macroscopic structure may be transparent and may be two-dimensional, or three-dimensional. Typically each dimension is at least 10 μm, in size. In certain embodiments, at least two dimensions are at least 100 μm, or at least 1000 μm in size. Frequently at least two dimensions are at least 1-10 mm in size, 10-100 mm in size, or more.

In certain embodiments, the size of the filaments may be about 10 nanometers (nm) to about 20 nm. The interfilament distance may be about 50 nm to about 80 nm. In some embodiments, the size of the filaments, for example, the diameter of the filaments, may be about 5 nm. In certain embodiments, the size of the filaments, for example, the diameter of the filaments, may be less than about 5 nm.

The peptides may also be complementary and structurally compatible. Complementary refers to the ability of the peptides to interact through ionized pairs and/or hydrogen bonds which form between their hydrophilic side-chains, and structurally compatible refers to the ability of complementary peptides to maintain a constant distance between their peptide backbones. Peptides having these properties participate in intermolecular interactions which result in the formation and stabilization of beta-sheets at the secondary structure level and interwoven filaments at the tertiary structure level.

Both homogeneous and heterogeneous mixtures of peptides characterized by the above-mentioned properties may form stable macroscopic membranes, filaments, and hydrogels. Peptides which are self-complementary and self-compatible may form membranes, filaments, and hydrogels in a homogeneous mixture. Heterogeneous peptides, including those which cannot form membranes, filaments, and hydrogels in homogeneous solutions, which are complementary and/or structurally compatible with each other may also self-assemble into macroscopic membranes, filaments, and hydrogels.

The membranes, filaments, and hydrogels may be non-cytotoxic. The hydrogels of the present disclosure may be digested and metabolized in a subject. The hydrogels may be biodegraded in 30 days or less. The hydrogels have a simple composition, are permeable, and are relatively inexpensive to produce in large quantities. The membranes and filaments, hydrogels or scaffolds may also be produced and stored in a sterile condition. The optimal lengths for membrane formation may vary with at least one of the amino acid composition, solution conditions, and conditions at the site of formation.

The self-assembly of the peptides may be attributable to hydrogen bonding and hydrophobic bonding between the peptide molecules by the amino acids composing the peptides.

The self-assembling peptides of the present disclosure may have a nanofiber diameter in a range of about 10 nm to about 20 nm and an average pore size is in a range of about 5 nm to about 200 nm. In some embodiments, the self-assembling peptides of the present disclosure may have a nanofiber diameter of about 5 nm or less than about 5 nm. In certain embodiments, the nanofiber diameter, the pore size, and the nanofiber density may be controlled by at least one of the concentration of peptide solution used and the amount of peptide solution used, such as the volume of peptide solution.

The self-assembling peptides of the present disclosure, such as ST14 and T14, may be peptide sequences that lack a distinct physiologically or biologically active motif or sequence, and therefore may not impair intrinsic cell function. Physiologically active motifs may control numerous intracellular phenomena such as transcription, and the presence of physiologically active motifs may lead to phosphorylation of intracytoplasmic or cell surface proteins by enzymes that recognize the motifs. When a physiologically active motif is present, transcription of proteins with various functions may be activated or suppressed. The self-assembling peptides of the present disclosure may lack such physiologically active motifs and therefore do not carry this risk. A sugar may be added to the self-assembling peptide solution to improve the osmotic pressure of the solution from hypotonicity to isotonicity, thereby allowing the biological safety to be increased. In certain examples, the sugar may be sucrose or glucose.

In accordance of one or more embodiments, a tonicity of the peptide solution may be hypotonic, isotonic, or hypertonic. In some specific non-limiting embodiments, the tonicity of the peptide solution may be isotonic. The tonicity of the peptide solution may be adjusted in various approaches. In some embodiments, the tonicity of the peptide solution may impact or adjust the tonicity associated with a site of administration of the peptide solution, such as but not limited to, an administration site associated with a subject such as a human body. For example, in some embodiments tonicity may be adjusted with a tonicity agent. The tonicity agent may be selected from the group consisting of but not limited to: dextrose, glycerin, mannitol, potassium chloride, and sodium chloride. In other embodiments, the tonicity of the peptide solution may be adjusted with at least one salt. The at least one salt may be selected from the group consisting of but not limited to: sodium chloride, potassium chloride, magnesium chloride, calcium chloride, and calcium sulfate. The at least one salt may include one or more salt forming cations and one or more salt forming anions. The one or more salt forming cations may be selected from the group consisting of but not limited to: ammonium, calcium, iron, magnesium, potassium, pyridinium, quaternary ammonium, and sodium. The one or more salt forming anions may be selected from the group consisting of but not limited to: acetate, carbonate, chloride, citrate, cyanide, fluoride, nitrate, nitrite, and phosphate.

The optimal lengths for membrane formation may vary with the amino acid composition. A stabilization factor contemplated by the peptides of the present disclosure is that complementary peptides maintain a constant distance between the peptide backbones.

The peptides can be chemically synthesized or they can be purified from natural and recombinant sources. Using chemically synthesized peptides may allow the peptide solutions to be deficient in unidentified components such as unidentified components derived from the extracellular matrix of another animal. This property therefore may eliminate concerns of infection, including risk of viral infection compared to conventional tissue-derived biomaterials. This may eliminate concerns of infection including infections such as bovine spongiform encephalopathy (BSE), making the peptide highly safe for medical use.

The initial concentration of the peptide may be a factor in the size and thickness of the membrane, hydrogel, or scaffold formed. In general, the higher the peptide concentration, the higher the extent of membrane or hydrogel formation. Hydrogels, or scaffolds, formed at higher initial peptide concentrations (about 10 mg/ml) (about 1.0 w/v percent) may be thicker and thus, likely to be stronger.

Formation of membranes, hydrogels, or scaffolds may occur based on the exposure of the peptide solution to select conditions. Formation of the membranes, hydrogels, or scaffolds may occur in a range on the order of seconds to on the order of minutes. For example, the formation may be instantaneous. In some embodiments, the formation may occur in less than 1 second. The formation may occur in less than 5 seconds, less than 30 seconds, less than 1 minute, less than 5 minutes, less than 15 minutes, or less than 30 minutes. The formation of the hydrogel may occur within about one to two minutes. In other examples, the formation of the hydrogel may occur within about three to four minutes. In certain embodiments, the formation of the membranes or hydrogels may be reversible, and in other embodiments, the formation may be irreversible. In certain embodiments the time it takes to form the hydrogel may be based at least in part on one or more of the concentration of the peptide solution, the volume of peptide solution applied, and the conditions at the area of application (for example, the concentration of monovalent metal cations at the area of application, the pH of the area, and the presence of one or more fluids at or near the area). The process may be unaffected by pH of less than or equal to 12, and by temperature. The membranes or hydrogels may form at temperatures in the range of about 1 to 99 degrees Celsius.

In certain embodiments, the self-assembling peptide may be prepared with one or more components that may provide for enhanced effectiveness of the self-assembling peptide or may provide another action, treatment, therapy, or otherwise interact with one or more components of the subject. For example, additional peptides comprising one or more biologically or physiologically active amino acid sequences or motifs may be included as one of the components along with the self-assembling peptide. Other components may include biologically active compounds such as a drug or other treatment that may provide some benefit to a subject. For example, an antibiotic or small molecular drug to treat or prevent hemolysis, inflammation or infection may be administered with the self-assembling peptide, or may be administered separately.

The small molecular drugs may be selected from the group consisting of glucose, saccharose, purified saccharose, lactose, maltose, trehalose, destran, iodine, lysozyme chloride, dimethylisoprpylazulene, tretinoin tocoferil, povidone iodine, alprostadil alfadex, anise alcohol, isoamyl salicylate, $\alpha,\alpha$-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate. Other small molecular drugs may be contemplated. Protein-based drugs may be included as a component to be administered, and may include erythropoietin, tissue type plasminogen activator, synthetic hemoglobin and insulin.

A component may be included to protect the peptide solution against rapid or immediate formation into a hydrogel. This may include an encapsulated delivery system that may degrade over time to allow a controlled time release of the peptide solution into the target area to form the hydrogel over a desired, predetermined period of time. Biodegradable, biocompatible polymers may be used, such as ethylene vinyl acetate, polyanhydrides, polyglycolic acid, collagen, polyorthoesters, and polylactic acid.

Any of the components described herein may be included in the peptide solution or may be administered separate from the peptide solution. Additionally, any of the methods and methods of facilitating provided herein may be performed by one or more parties.

In some embodiments of the disclosure, the self-assembling peptides may be used as a coating on a device or an instrument. The self-assembling peptides may also be incorporated or secured to a support, such as gauze or a bandage, or a lining, that may provide a therapeutic effect to a subject, or that may be applied within a target area. The self-assembling peptides may also be soaked into a sponge for use.

The function and advantages of these and other embodiments of the compositions, peptides, peptide solutions, and methods disclosed herein will be more fully understood from the examples below. The following example is intended to illustrate the benefits of the disclosed compositions, but do not exemplify the full scope thereof.

EXAMPLES

Example 1: Morphological Studies

Atomic Force Microscopy (AFM) images of ST14 and T14 peptides were investigated to visualize their nano structures. Samples were prepared by placing an aliquot of approximately 50 microliters (μl) of the peptide (100 micromolar (μM)) solution on the surface (9 millimeters (mm) in diameter) of a mica surface. Each sample was left on the mica for about 30 seconds (s) and then rinsed with aliquots of 100 μl of Milli-Q (ultrapure) water to remove unattached peptides. The sample on the mica surface was then air-dried for AFM observation. AFM was performed with Asylum-1

MFP-3D AFM System (Asylum Research, Santa Barbara, Calif.) using a tapping mode. The images utilized an Olympus Si tip (AC240FS). The cantilever's free resonance frequency was 70 kHz. Height images were recorded with 256×256 pixels resolution.

Figure 3:
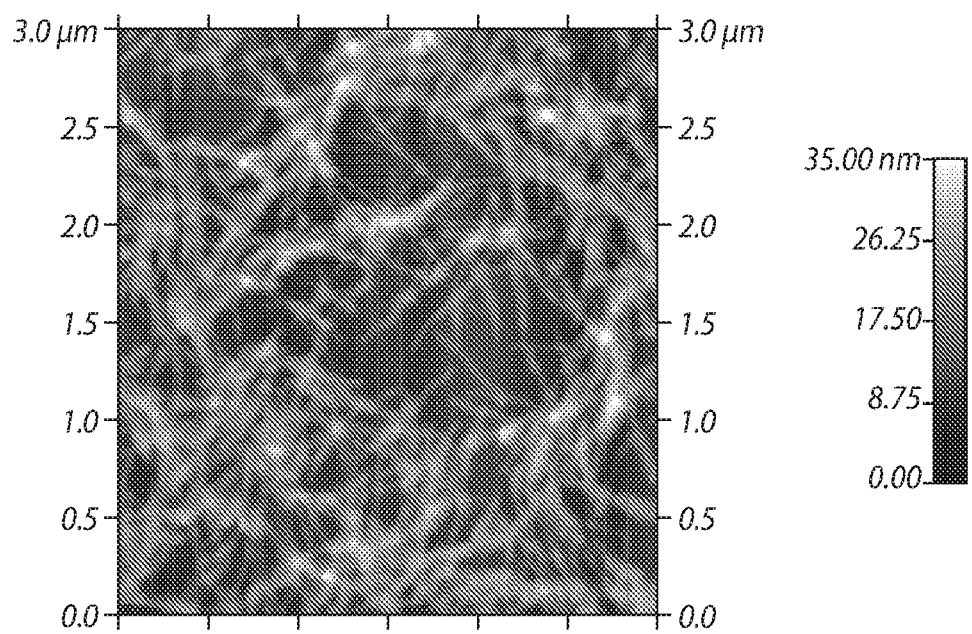
FIG. 3 is an image of peptide ST14 (SEQ ID NO: 2), in accordance with some embodiments.
Figure 4:
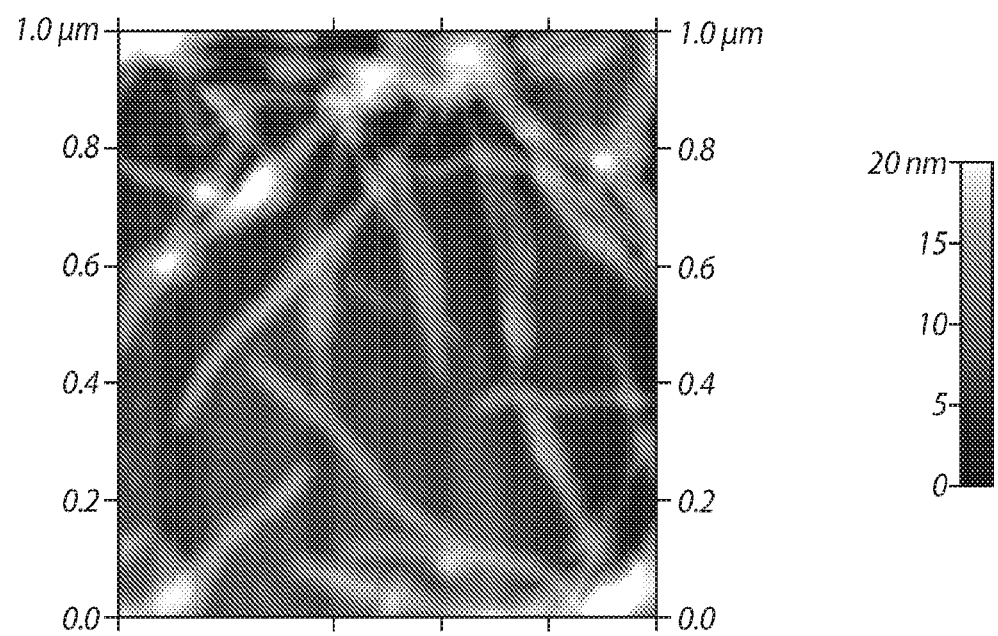
FIG. 4 is an image of peptide ST14 (SEQ ID NO: 2), in accordance with some embodiments.
Figure 5:
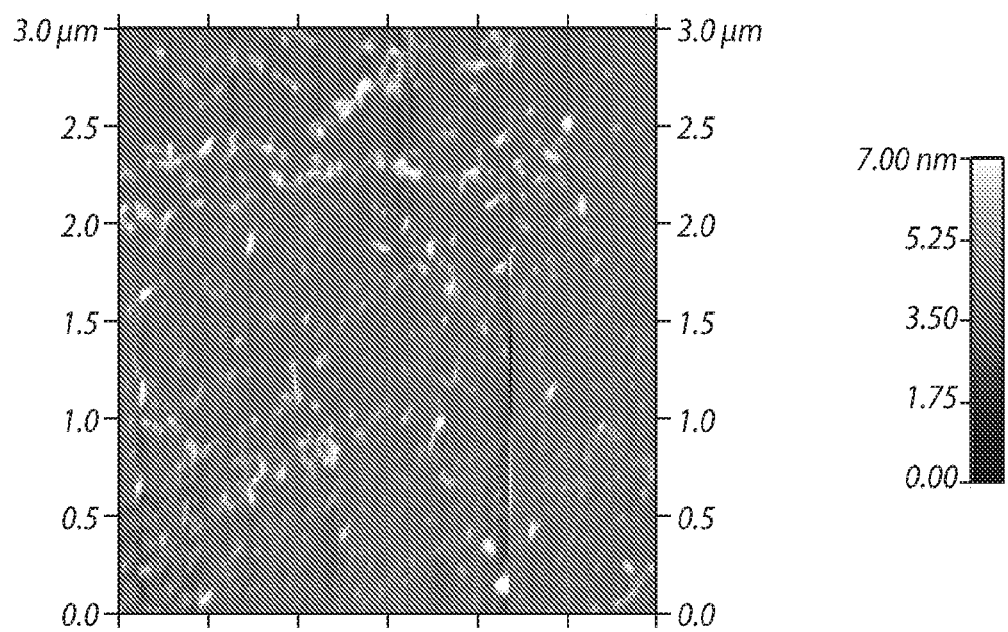
FIG. 5 is an image of peptide T14 (SEQ ID NO:1), in accordance with some embodiments.
Figure 6:
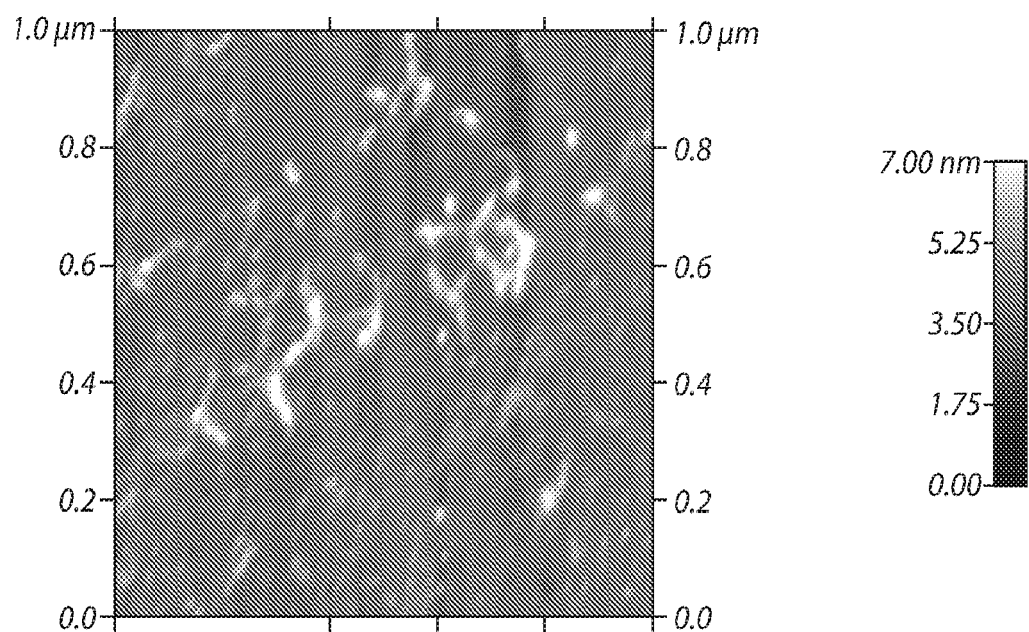
FIG. 6 is an image of peptide T14 (SEQ ID NO:1), in accordance with some embodiments.

As shown in FIGS. 3 and 4, AFM morphological studies demonstrated that ST14 forms self-assembled nanofibers. Aggregates have been detected in T14, as shown in FIGS. 5 and 6.

Example 2: Stability and Sterilization Studies

Sterilization is a very important step in the manufacturing process for all biomaterials, including the self-assembling peptide solutions. Autoclave treatment of the peptides appears to be the best sterilization method for highly viscous peptide solutions for which filtration sterilization might not be possible. To determine if autoclaving degrades peptide molecules, mass spectrometry (mass spec) analysis of peptides was performed before and after autoclave at 121° C. for 25 min at high pressure saturated steam. The results are shown in FIGS. 7-8 and FIGS. 9-10 for ST14 and T14, respectively, wherein the N-terminus and the C-terminus are not protected.

Figure 7:
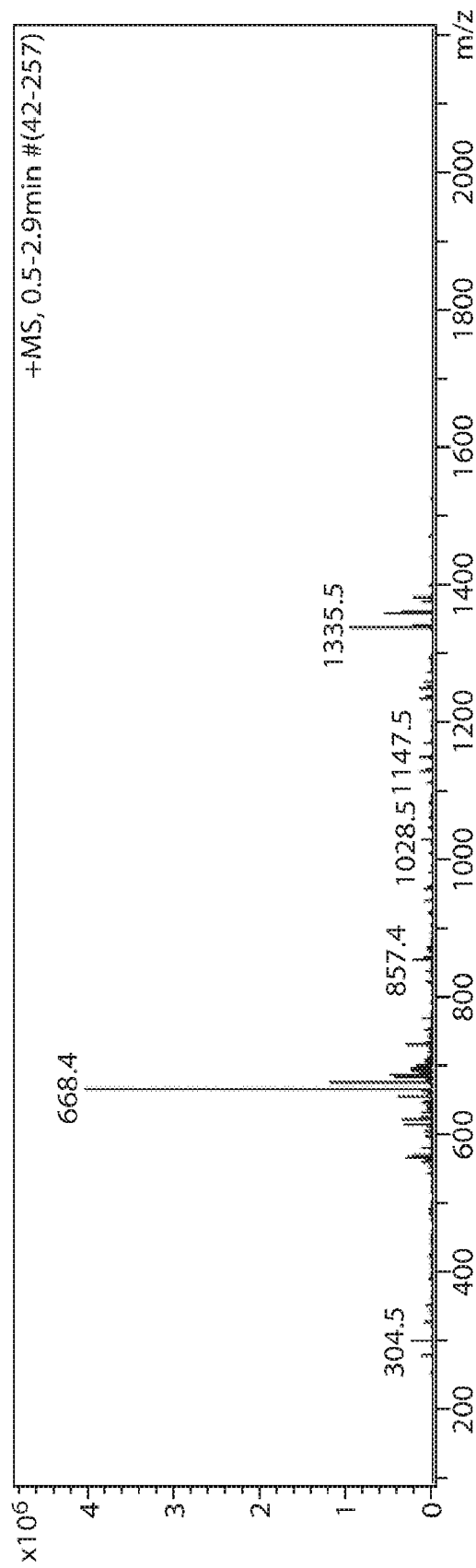
FIG. 7 is a graph of mass spectrometry of peptide ST14 (SEQ ID NO: 2), in accordance with some embodiments.
Figure 8:
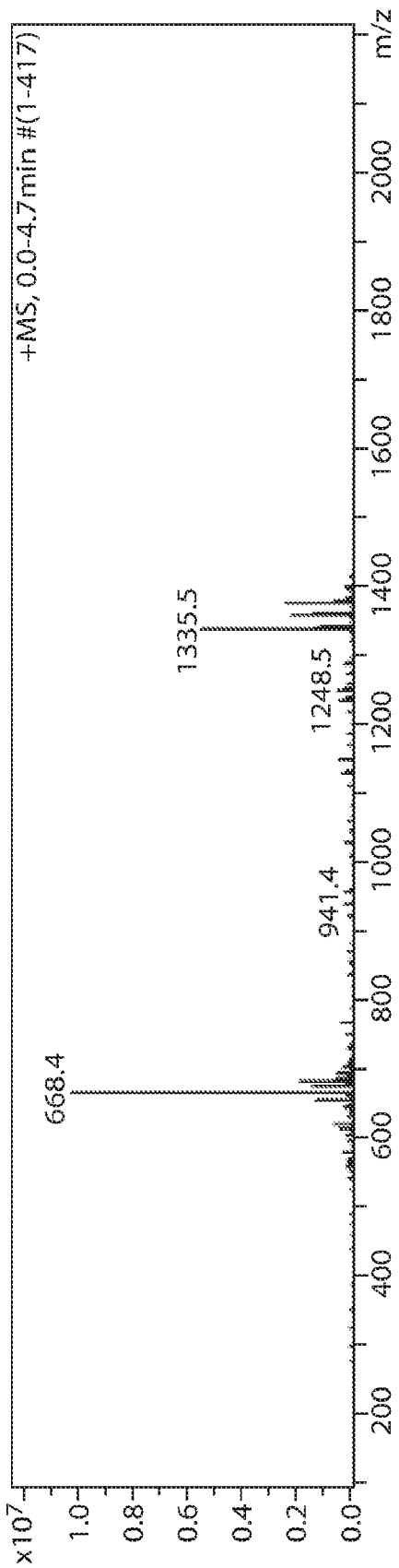
FIG. 8 is a graph of mass spectrometry of peptide ST14 (SEQ ID NO: 2), in accordance with some embodiments.

The measured molar mass of ST14, prior to autoclave treatment, was 1335, which matches the calculated molar mass (FIGS. 7-8). ST14 did not degrade during autoclave treatment, therefore autoclave is an appropriate method for sterilization of ST14.

Figure 9:
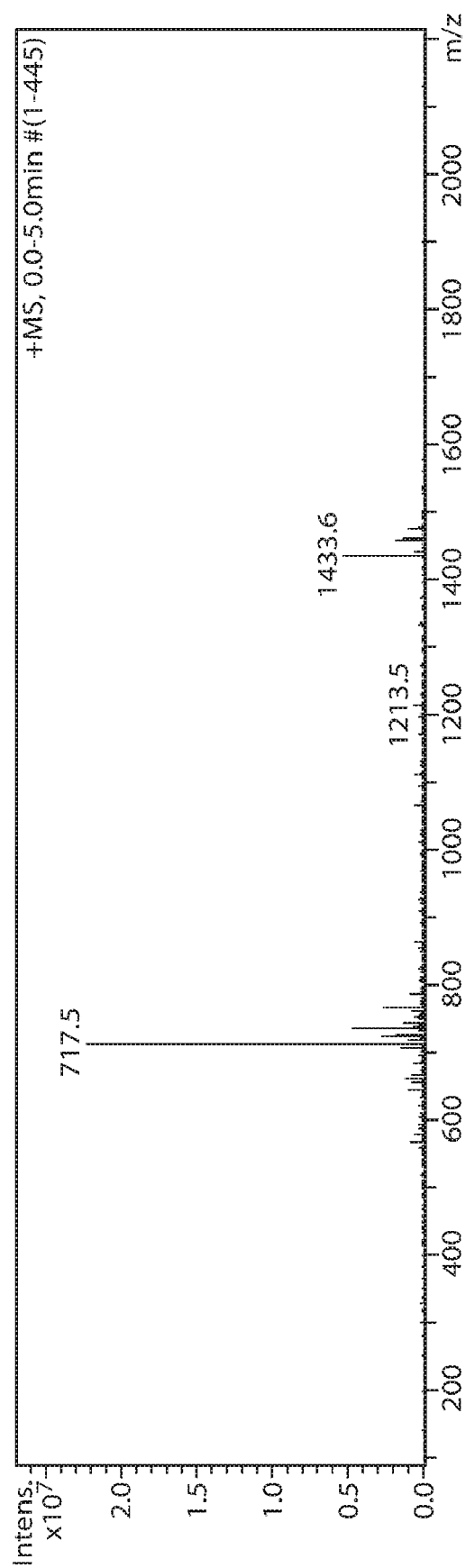
FIG. 9 is a graph of mass spectrometry of peptide T14 (SEQ ID NO:1), in accordance with some embodiments.
Figure 10:
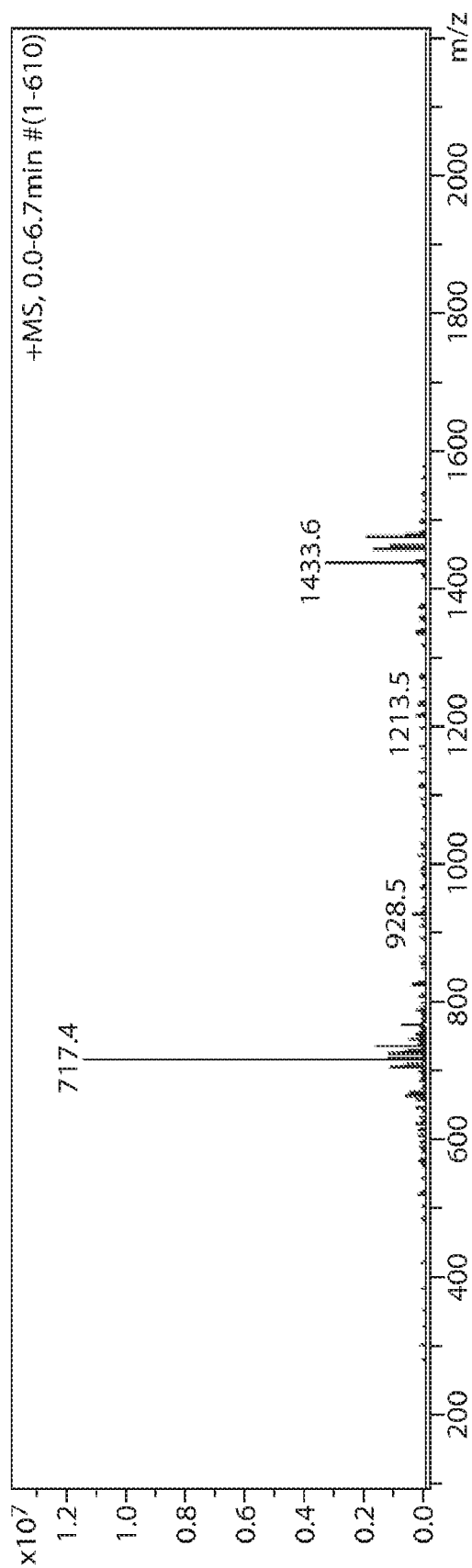
FIG. 10 is a graph of mass spectrometry of peptide T14 (SEQ ID NO:1), in accordance with some embodiments.

The measured molar mass of T14 is 1433, which matches the calculated molar mass. T14 did not degrade during autoclave, therefore autoclave treatment is an appropriate method for sterilization of T14, as shown in FIGS. 9-10.

Example 3: Peptide Solution Visual Appearance

ST14 and T14 were tested for dissolution in deionized water and appearance in solution at various concentrations. ST14 and T14 solutions were translucent at 1 percent, weight per volume (w/v) to 5 percent w/v. ST14 formed thick solutions at 1 percent, weight per volume (w/v) to 5 percent w/v, while T14 formed a thick solution at 5 percent w/v. This shows a difference between the two peptides that may indicate how they may behave under given conditions.

Example 4: pH of Peptide Solutions

The pH of the peptides in deionized water to provide a peptide solution were measured at various concentrations. The pH of the peptide solutions was measured at various concentrations. ST14 and T14 were tested. The recorded pH values ranged from about 1.9 to about 2.5. The results are listed in Table 2. These results show that the pH varies, depending on the concentration of peptide and the type of peptide.

TABLE 2 pH values of ST14 and T14 at various concentrations.

| Peptide | Concentration | pH |
|---|---|---|
| ST14 | 2.5% | 1.9 |
|  | 2.0% | 2.0 |
|  | 1.5% | 2.1 |
|  | 1.0% | 2.2 |
|  | 0.5% | 2.5 |

TABLE 2-continued pH values of ST14 and T14 at various concentrations.

| Peptide | Concentration | pH |
|---|---|---|
| T14 | 2.5% | 2.0 |
|  | 2.0% | 2.1 |
|  | 1.5% | 2.2 |
|  | 1.0% | 2.3 |
|  | 0.5% | 2.5 |

Example 5: Peptide Gel Formation

A Congo Red assay was performed to determine gel formation of peptide solutions in a PBS buffer solution (pH 7.4). 100 μl of each gel at varying concentrations were plated on a glass slide. After 30 seconds, 500 μl of a 1% Congo Red solution in PBS buffer (pH 7.4) was added around and on top of each of the gel aliquots and then the excess Congo Red solution was wiped off prior to examination.

Figure 11:
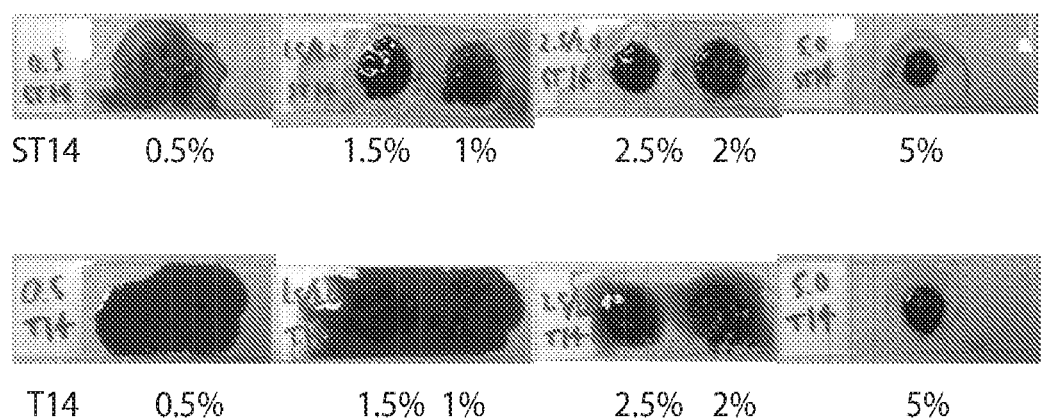
FIG. 11 are images related to gel formation with Congo Red buffer solution, in accordance with some embodiments.

ST14 and T14 were plated at varying concentrations of 0.5%, 1.0%, 1.5%, 2.0%, 2.5% and 5.0%. Visualization of gel formation determined the success or failure of gelation at each concentration. ST14 did not form a gel at 0.5%. T14 did not form a gel below 1%. The data are shown in FIG. 11.

Example 6: Effect of Concentration on the Rheological Properties

The rheological properties of the ST14 were evaluated at various concentrations using a rheometer (AR500, TA Instruments) with 40 mm plates. Peptide solution (700 μL) was placed on the rheometer plate and excess solution was gently removed by Kimwipes; measurements were performed after 2 minutes of relaxation time at 37° C. The storage modulus, loss modulus, and viscosity ($\eta'$) were measured at 37° C. with the plates placed at a measuring geometry gap of 300 μm, and stress sweep tests were performed at 0.1 Pa~1000 Pa of oscillation stress with angular frequency at 10 rad/s.

Figure 12:
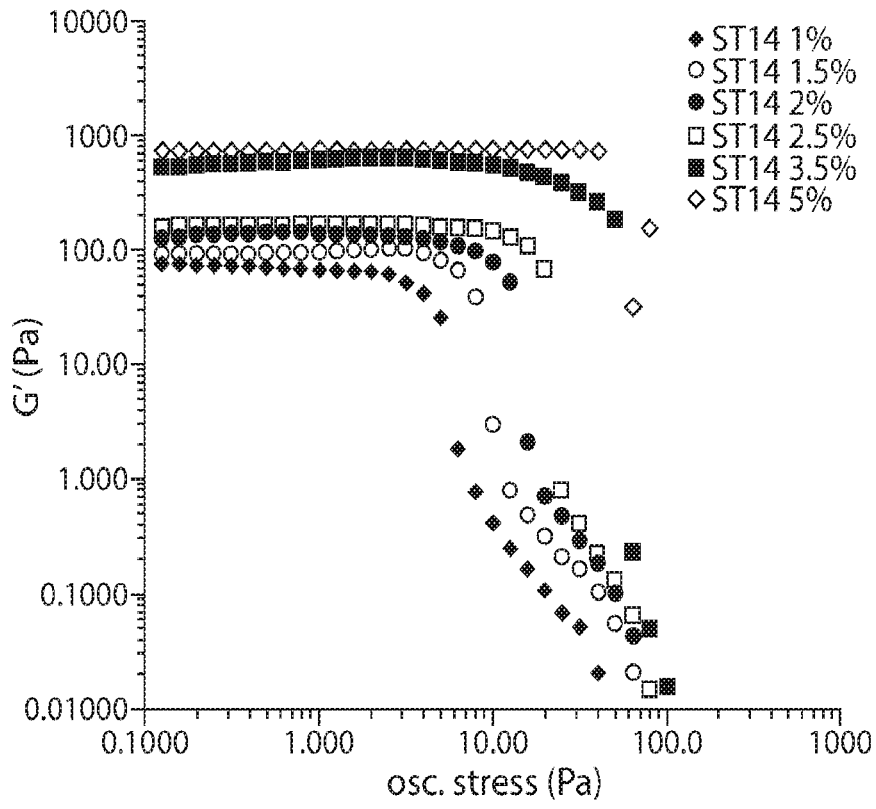
FIG. 12 is a graph plotting storage modulus versus oscillation stress of ST14 (SEQ ID NO: 2), in accordance with some embodiments.
Figure 13:
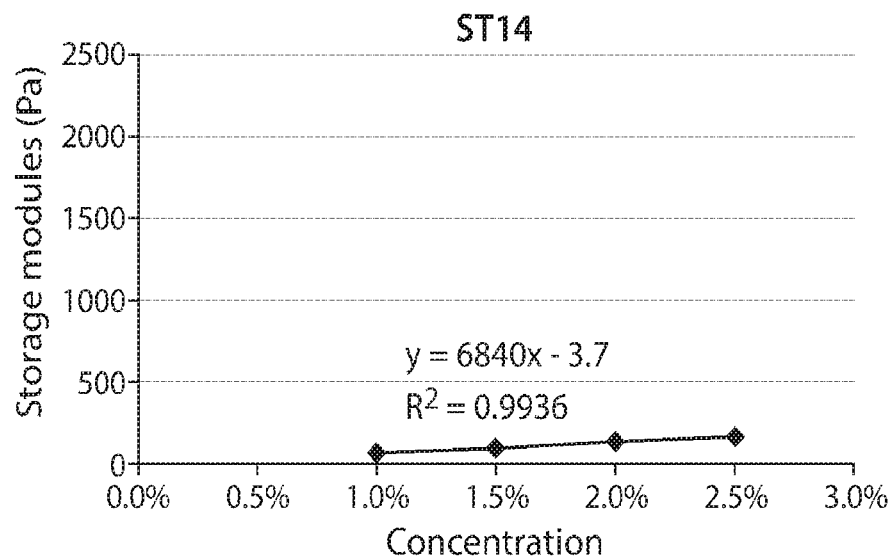
FIG. 13 is a graph plotting storage modulus versus concentration of ST14 (SEQ ID NO: 2), in accordance with some embodiments.

The rheology results are shown in FIGS. 12 and 13 for ST14. The rheological properties of T14 were not measured. Rheological properties of ST14 at various concentrations is also shown in Table 3.

The storage modulus, yield stress, and max. viscosity of ST14 increased with increasing concentration.

TABLE 3

Rheological properties of ST14

| Concentration | Storage Modulus (G')* (Pa) | Loss Modulus (G')* (Pa) | Yield Stress (Pa)* | Max. Viscosity (max $\eta'$) (Pa-s)* |
|---|---|---|---|---|
| 1 | 67 | 11.4 | 5.0 | 1.2 |
| 1.5 | 94 | 9.8 | 7.9 | 1.5 |
| 2 | 136 | 17.3 | 10.0 | 2.0 |
| 2.5 | 167 | 17.1 | 15.9 | 2.2 |

*At 1 Pa of oscillation stress

Example 7: Effect of Cell Culture Medium Contact on the Peptide Hydrogel Properties The effects of Dulbecco's modified Eagle's medium (DMEM) (pH 7.4) on the rheological properties of ST14 were evaluated on a rheometer (AR500, TA Instruments) with 40 mm plates. DMEM is a cell culture medium that contains 6.4 g/L of NaCl, 3.4 g/L NaHCO$_3$ (sodium bicarbonate), minor amounts of other salts, various amino acids, and 4.5 g/L of glucose. The pH of DMEM is 7.2±0.2 and the osmolality is 335±30 mOsm/Kg H$_2$O; both measurements are close to human physiological fluids such as blood. Peptide solutions (1%) were kept in 4° C. for at least 48 hours before testing. To perform the experiment, 1 mL of peptide solution was gently pipetted and placed on the plate of the rheometer. 2 mL of DMEM solution was gently added around the peptide solution. The peptide solution was treated with DMEM for two minutes, then the media was removed, and the plates were placed at a measuring geometry gap at around 450 μm. Measurements were performed at 37° C. after 2 min of relaxation time. Frequency tests were performed from 1 rad/s to 100 rad/s at 1 Pa of oscillation stress.

Figure 14:
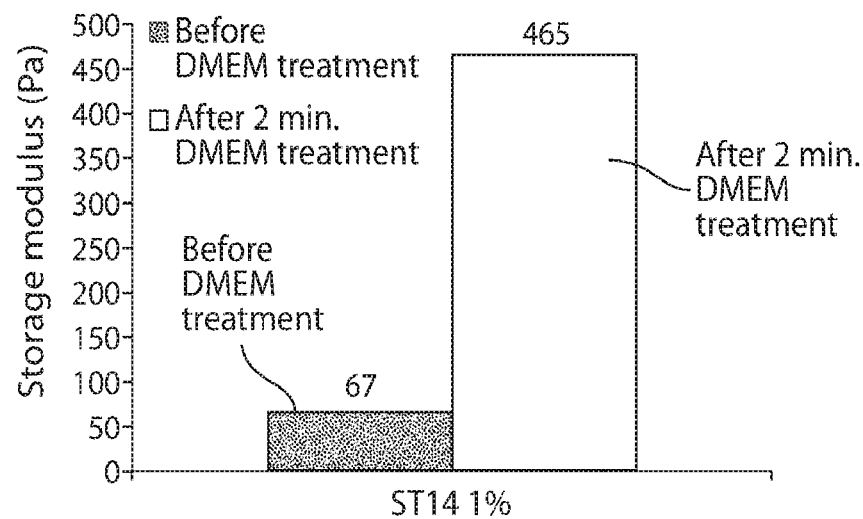
FIG. 14 is a graph plotting storage modulus of ST14 (SEQ ID NO: 2) before and after DMEM treatment, in accordance with some embodiments.
Figure 15:
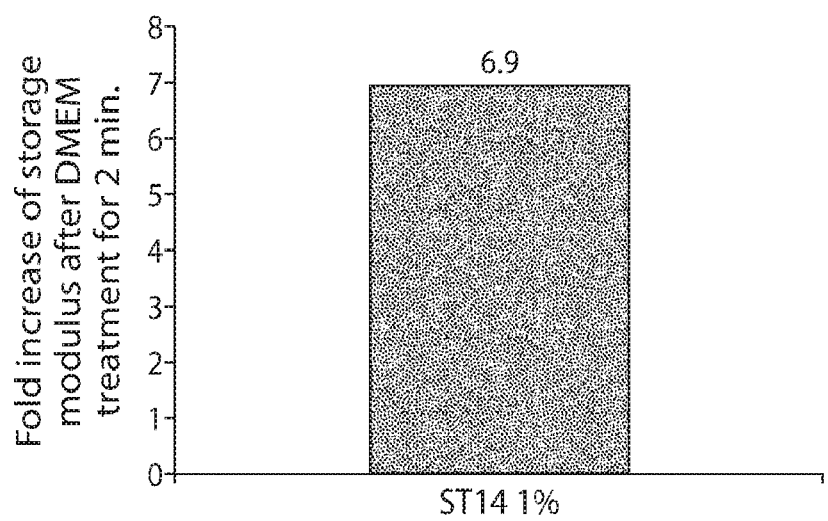
FIG. 15 is a graph plotting fold increase of storage modulus of ST14 (SEQ ID NO: 2) after DMEM treatment, in accordance with some embodiments.

The theological properties of ST14 (1%) were compared before and after DMEM treatment for 2 minutes in FIG. 14. Storage modulus data for untreated peptide solutions were taken from the data at 1 Pa and 10 rad/s in their stress sweep tests, and those for DMEM-treated peptide hydrogels were adapted from the data at 1 Pa and 10 rad/s in their frequency sweep test. The fold increase of storage moduli after DMEM treatment for 2 minutes is shown in FIG. 15. ST14 showed 6.9 fold increase of storage moduli after DMEM treatment.

This observation suggests that a critical intermolecular interaction arises after DMEM treatment, which determines the final stiffness after DMEM treatment. The change in pH and salt concentration may affect its rheological properties.

Example 8: Cell Viability Test

A cell viability (cytotoxicity) assay was performed to measure the ability of ST14 to support the viability of C57 BL/6 Mouse Mesenchymal Stem Cells (mMSCs)—a frequently—used cell line in hydrogel tissue culture systems. Each hydrogel was prepared at a concentration of 2.5% and then diluted to concentrations of 1.5%, 1.25%, 1.0%, 0.75%, and 0.50% with sucrose, so that the final concentration of sucrose was 10%. Cells were washed and re-suspended in 10% sucrose to a final concentration of 5 million cells/ml. Cells were centrifuged and the supernatant was removed. The cells were re-suspended in each of the concentrations of hydrogels in 10% sucrose. The protocol was then followed for plating drop cultures and subsequent isolation as described in the PuraMatrix® Guidelines for Use (BD/Corning website).

Figure 16:
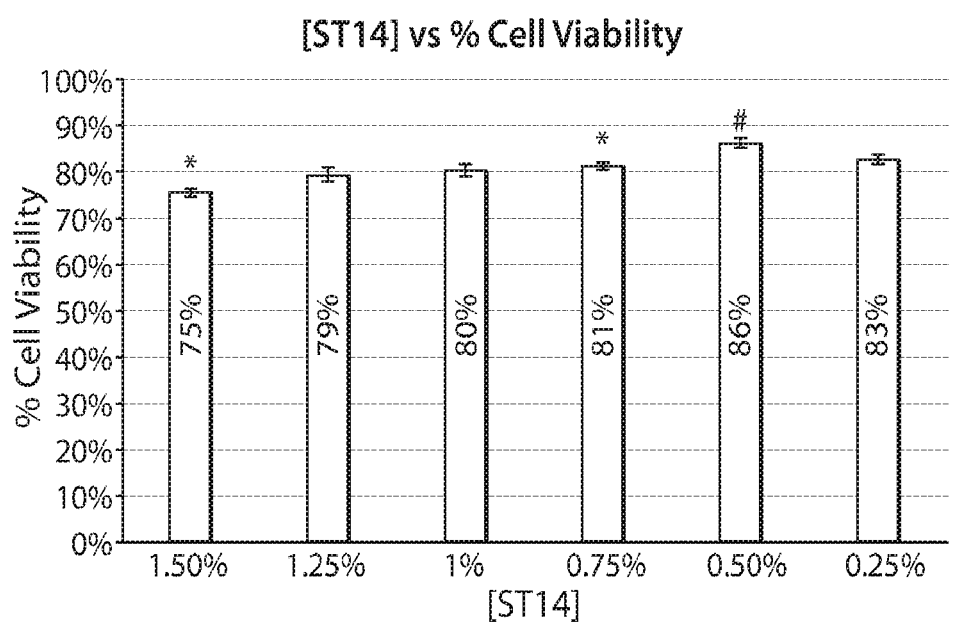
FIG. 16 is a graph plotting percent cell viability versus concentration of peptide, in accordance with some embodiments.

The results are shown in FIG. 16 for ST14. Cell viabilities significantly decreased when the concentration of peptides was over 0.75%.

In FIG. 16, "*" is noted when the cell viability is significantly lower than the cell viability at next lower concentration (p<0.05), and "#" is noted when the cell viability is significantly higher than the cell viability at next lower concentration (p<0.05).

The invention claimed is:
1. A peptide solution comprising a self-assembling peptide, consisting of a chemical structure (ST14) (SEQ ID NO: 2) of:

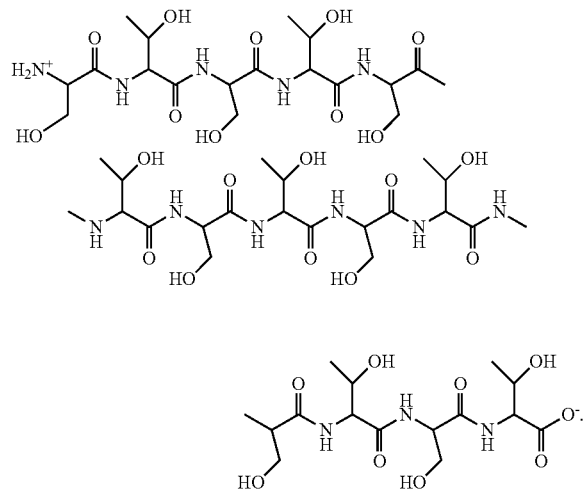

2. The peptide solution of claim 1, wherein the self-assembling peptide is capable of forming self-assembled nanofibers.
3. The peptide solution of claim 1, wherein a concentration of the self-assembling peptide in the peptide solution is between about 0.1 weight per volume (w/v) percent to about 10 weight per volume (w/v) percent.
4. The peptide solution of claim 3, wherein the concentration of the self-assembling peptide in the peptide solution is between about 0.5 weight per volume (w/v) percent and about 5 weight per volume (w/v) percent.
5. The peptide solution of claim 1, wherein a pH of the peptide solution is between about 0.5 and about 8.
6. The peptide solution of claim 5, wherein the pH of the peptide solution is between about 3 to about 7.
7. The peptide solution of claim 1, wherein a tonicity of the peptide solution is hypotonic, isotonic, or hypertonic.
8. The peptide solution of claim 7, wherein the tonicity of the peptide solution is isotonic.
9. The peptide solution of claim 7, wherein the tonicity of the peptide solution is adjusted with a tonicity agent selected from the group consisting of: dextrose, glycerin, mannitol, potassium chloride, and sodium chloride.
10. The peptide solution of claim 7, wherein the tonicity of the peptide solution is adjusted with at least one salt selected from the group consisting of: sodium chloride, potassium chloride, magnesium chloride, calcium chloride, and calcium sulfate.
11. The peptide solution of claim 10, wherein the at least one salt comprises one or more salt forming cations and one or more salt forming anions, wherein the one or more salt forming cations is selected from the group consisting of: ammonium, calcium, iron, magnesium, potassium, pyridinium, quaternary ammonium, and sodium, and wherein the one or more salt forming anions is selected from the group consisting of: acetate, carbonate, chloride, citrate, cyanide, fluoride, nitrate, nitrite, and phosphate.
12. The peptide solution of claim 1, further comprising human cells.
13. The peptide solution of claim 12, having a cell concentration of about 5 million cells per milliliter.
14. The peptide solution of claim 1, wherein the peptide solution has a storage modulus and the storage modulus increases between about 5 to about 10 times after exposure to a neutral pH.
15. The peptide solution of claim 14, wherein the storage modulus of the peptide solution increases about 7 times after exposure to a neutral pH.
16. A method for sterilizing peptides comprising:
providing a peptide solution comprising a self-assembling peptide consisting of a chemical structure (ST14) (SEQ ID NO: 2) of:

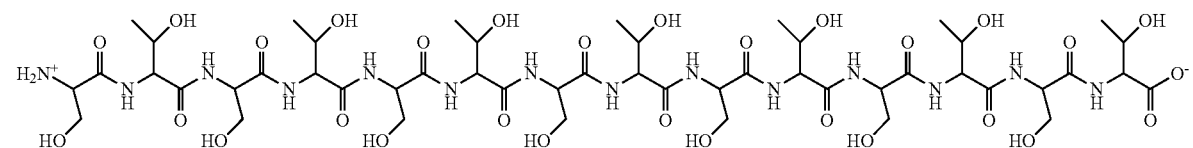 [SMILES: CC(O)C(NC(=O)C(CO)NC(=O)C(NC(=O)C(CO)NC(=O)C(NC(=O)C(CO)NC(=O)C(NC(=O)C(CO)NC(=O)C(NC(=O)C(CO)NC(=O)C(NC(=O)C(CO)NC(=O)C(NC(=O)C([NH3+])CO)C(C)O)C(C)O)C(C)O)C(C)O)C(C)O)C(C)O)C(=O)[O-]]

or a chemical structure (T14) (SEQ ID NO: 1) of:

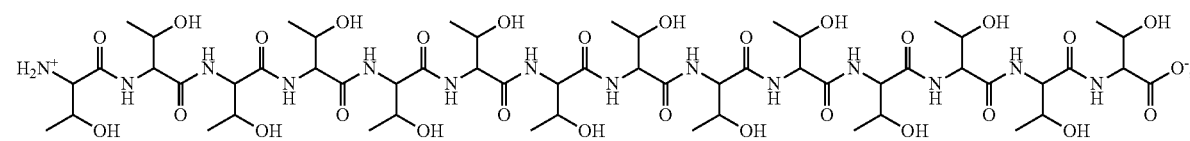

treating the peptide solution at a predetermined temperature and a predetermined pressure for a predetermined period of time to sterilize the peptide solution, the predetermined temperature and predetermined pressure selected to provide conditions of saturated steam.

17. The method of claim 16, further comprising measuring the molar mass of the self-assembling peptide in the peptide solution prior to treating the peptide solution.

18. The method of claim 17, further comprising measuring the molar mass of the self-assembling peptide in the peptide solution subsequent to treating the peptide solution.

19. The method of claim 18, further comprising comparing the molar mass of the self-assembling peptide in the peptide solution prior to treating the peptide solution, with the molar mass of the self-assembling peptide in the peptide solution subsequent to treating the peptide solution.

20. The method of claim 16, wherein treating the peptide solution comprises treating the peptide solution in an autoclave.

21. A peptide solution comprising a self-assembling peptide, consisting of a chemical structure (T14) (SEQ ID NO: 1) of:

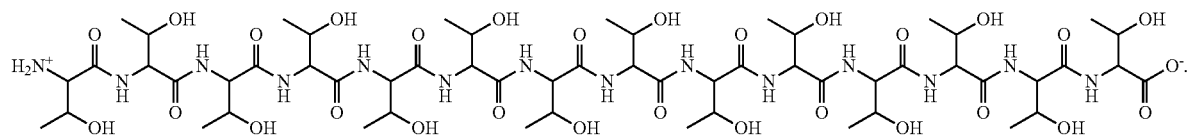

22. The peptide solution of claim 21, wherein the self-assembling peptide is capable of forming self-assembled nanofibers.

23. The peptide solution of claim 21, wherein a concentration of the self-assembling peptide in the peptide solution is between about 0.1 weight per volume (w/v) percent to about 10 weight per volume (w/v) percent.

24. The peptide solution of claim 23, wherein the concentration of the self-assembling peptide in the peptide solution is between about 0.5 weight per volume (w/v) percent and about 5 weight per volume (w/v) percent.

25. The peptide solution of claim 21, wherein a pH of the peptide solution is between about 0.5 and about 8.

26. The peptide solution of claim 25, wherein the pH of the peptide solution is between about 3 to about 7.

27. The peptide solution of claim 21, wherein a tonicity of the peptide solution is hypotonic, isotonic, or hypertonic.

28. The peptide solution of claim 27, wherein the tonicity of the peptide solution is isotonic.

29. The peptide solution of claim 27, wherein the tonicity of the peptide solution is adjusted with a tonicity agent selected from the group consisting of: dextrose, glycerin, mannitol, potassium chloride, and sodium chloride.

30. The peptide solution of claim 27, wherein the tonicity of the peptide solution is adjusted with at least one salt selected from the group consisting of: sodium chloride, potassium chloride, magnesium chloride, calcium chloride, and calcium sulfate.

31. The peptide solution of claim 30, wherein the at least one salt comprises one or more salt forming cations and one or more salt forming anions, wherein the one or more salt forming cations is selected from the group consisting of: ammonium, calcium, iron, magnesium, potassium, pyridinium, quaternary ammonium, and sodium, and wherein the one or more salt forming anions is selected from the group consisting of: acetate, carbonate, chloride, citrate, cyanide, fluoride, nitrate, nitrite, and phosphate.

32. The peptide solution of claim 21, further comprising human cells.

33. The peptide solution of claim 32, having a cell concentration of about 5 million cells per milliliter.

34. The peptide solution of claim 21, wherein the peptide solution has a storage modulus and the storage modulus increases between about 5 to about 10 times after exposure to a neutral pH.

35. The peptide solution of claim 34, wherein the storage modulus of the peptide solution increases about 7 times after exposure to a neutral pH.

* * * * *

SEQUENCE LISTING

<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: Synthetically generated oligopeptide

<400> SEQUENCE: 1

Thr Thr Thr Thr Thr Thr Thr Thr Thr Thr Thr Thr Thr Thr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated oligopeptide

<400> SEQUENCE: 2

Ser Thr Ser Thr Ser Thr Ser Thr Ser Thr Ser Thr Ser Thr
1               5                   10